US009028449B2

(12) United States Patent
DeLegge

(10) Patent No.: US 9,028,449 B2
(45) Date of Patent: May 12, 2015

(54) DEVICE, KIT AND METHOD FOR PLACING JEJUNAL TUBE DEVICE THROUGH STOMACH AND INTO SMALL INTESTINE

(71) Applicant: DeLegge Medical, Inc., Mt. Pleasant, SC (US)

(72) Inventor: Rebecca L. DeLegge, Mt. Pleasant, SC (US)

(73) Assignee: DeLegge Medical, Inc., Mt. Pleasant, SC (US)

( * ) Notice: Subject to any disclaimer, the term of this patent is extended or adjusted under 35 U.S.C. 154(b) by 38 days.

(21) Appl. No.: 13/793,494

(22) Filed: Mar. 11, 2013

(65) Prior Publication Data

US 2013/0289523 A1   Oct. 31, 2013

Related U.S. Application Data

(60) Provisional application No. 61/638,235, filed on Apr. 25, 2012.

(51) Int. Cl.
*A61M 5/32* (2006.01)
*A61M 31/00* (2006.01)
*A61J 15/00* (2006.01)
*A61B 17/34* (2006.01)

(52) U.S. Cl.
CPC ......... *A61J 15/0038* (2013.01); *A61B 17/3415* (2013.01); *A61J 15/0069* (2013.01); *A61J 15/0019* (2013.01)

(58) Field of Classification Search
CPC .................. A61B 17/3415; A61B 2017/00349; A61J 15/0015; A61J 15/0069; A61J 15/0007; A61J 15/0023; A61J 15/0019

USPC .......................................... 604/910, 174, 506
See application file for complete search history.

(56) References Cited

U.S. PATENT DOCUMENTS

| 5,037,387 A | 8/1991 | Quinn et al. |
| 5,259,367 A * | 11/1993 | Kirby et al. .................. 604/175 |
| 5,334,185 A | 8/1994 | Giesy et al. |
| 8,473,034 B2 * | 6/2013 | Cage et al. .................. 600/424 |
| 2003/0171718 A1 * | 9/2003 | DeLegge et al. ......... 604/164.01 |
| 2007/0167923 A1 | 7/2007 | Deal |
| 2010/0298812 A1 | 11/2010 | Wolkenstorfer |
| 2010/0305503 A1 | 12/2010 | Fang et al. |
| 2012/0226144 A1 * | 9/2012 | Cage et al. .................... 600/424 |

OTHER PUBLICATIONS

Notification of Transmittal of the International Search Report and the Written Opinion of the International Searching Authority, or the Declaration; dated Jul. 23, 2013; from corresponding application PCT/US2013/037907; 6p.

* cited by examiner

*Primary Examiner* — Rebecca E Eisenberg
(74) *Attorney, Agent, or Firm* — B. Craig Killough; Barnwell Whaley Patterson Helms

(57) ABSTRACT

A device and method for placing jejunal tube device through stomach and into small intestine with spring mechanism that is curled to diameter that is similar small bowel diameter, wherein the spring mechanism can be straightened during placement with a stiffening apparatus. The stiffening apparatus is guided by a forceps, and includes a retractable wire for use in attachment to the forceps. A c-plug is provided for centering jejunal tube during the placement procedure and to facilitate insufflation, the c-plug being split about midline to facilitate removal of the c-plug after tube placement.

16 Claims, 11 Drawing Sheets

DEVICE, KIT AND METHOD FOR PLACING JEJUNAL TUBE DEVICE THROUGH STOMACH AND INTO SMALL INTESTINE

RELATED APPLICATION

This application claims the benefit of priority from U.S. Provisional Application No. 61/638,235, filed Apr. 25, 2012, and titled "A Device, Kit and Method for Placing Jejunal Tube Device Through Stomach and Into Small Intestine", the contents of which is incorporated herein by reference.

TECHNICAL FIELD

The present invention relates generally to the field of feeding tubes and more specifically to a device and method for placing Jejunal feeding tube devices through stomach and into small intestine.

BACKGROUND OF THE INVENTION

Placement of a Jejunal feeding tube through a previously placed PEG or gastrostomy tube has been difficult at best. The current techniques, such as the wire guide method and the drag and pull method, are full of challenges from both the method and device perspective.

The wire guide technique utilizes an airplug to fit over a 0.035" wire guide that is threaded through a PEG tube and grasped with a biopsy forceps. This method requires that the stomach be filled with air while the endoscope, forceps and wire guide are advanced into the small bowel before the airplug can be removed from the wire guide. Following the airplug removal, a Jejunal feeding tube, also referred to as a jtube, is pushed over the wire guide, through the PEG tube and into place in the small bowel. The forceps holds the distal end of the wire guide within the small bowel during advancement of the jtube. Once the end of the jtube is positioned within the small bowel, the forceps may be uncouple from the wire guide. Thereafter, the wire guide may be removed from the jtube. The forceps is typically left in place while the endoscope is removed from the patient to help hold the jtube in place while the wire guide is removed.

There are several drawbacks to the wire guide method. For example, during removal of the forceps from the wire guide or jtube, the jtube is often dragged back into the stomach. If this occurs, then the procedure must be restarted. In addition, care must be taken to maintain tension on the wire guide during the placement procedure. If adequate tension is not maintained, then the jtube may inadvertently curl within the stomach during or subsequent to removal of the wire guide.

The grab and pull method for Jejunal tube placement likewise has drawbacks and is often unsuccessful. This technique involves pushing a jtube with a thin line (like fishing line) looped through the end thereof. A snare or biopsy forceps, which is advanced through an endoscope, is used to grasp the line. The endoscope and snare/forceps are then used to drag the jtube down into the small bowel. However, it is often difficult to detach the snare/forceps from the jtube without dislodging or removing the jtube from the small bowel. This is because the snare/forceps and jtube are usually covered with mucous and other biological material, which causes adhesion and friction between these components. In addition, the jtube, which is relatively flexible, will often loop within the stomach subsequent to placement, thereby pulling the end of the jtube out of the small bowel.

The drawbacks and shortcomings of the procedures described above are addressed by the novel devices and methods of the present invention.

BRIEF SUMMARY OF THE INVENTION

The present invention includes a jtube that is stiffened with a stiffening apparatus consisting of a stiff catheter with an outer hydrophilic coating and an inner drive wire with a loop configuration disposed on the distal end thereof. The loop is retractable within the jtube, which facilitates disconnection and separation of the loop from a forceps and/or a wire guide. The stiffening apparatus maintains the position of the jtube, and prevents the jtube from looping within the stomach as the endoscope, forceps and/or wire guide are retracted. The stiffening apparatus has an overall length that is slightly longer (for example, approximately 1 centimeter) than the length of the jtube. This allows the stiffener to extend slightly beyond the distal end of the jtube while the jtube is disposed within the stomach. The arrangement ensures that the forceps will be able to securely grasp the end of the stiffening apparatus during the placement procedure.

In one particular embodiment, the stiffening apparatus comprises an elongate mandrel with a wire loop extending distally from a distal end of the mandrel. The mandrel has a length that is shorter (for example, approximately 10 centimeters) than the length of the jtube. This shortened length provides increased flexibility to the distal end portion of the jtube while the stiffening apparatus is disposed therein, which reduces the possibility that the distal end of the jtube will perforate or cause damage to the stomach or small bowel during placement.

The present invention further includes a c-plug that is adapted to center the jtube within the PEG tube and fill any gaps there between, thereby creating a seal between the jtube and the PEG tube. This enables the stomach to be filled with air, thereby allowing an endoscope and forceps to be used to advance the jtube into the small bowel. The c-plug is removed as the distal end of the jtube is advanced and positioned within the small bowel. The c-plug is separable into two halves to facilitate its removal.

The present invention further includes a method of placing a jtube within the small bowel. First, the jtube and stiffening apparatus are advanced through an indwelling PEG tube. The c-plug is then positioned and fastened about the jtube and pushed into the PEG tube. Next, the stiffening apparatus is advanced towards the end of the jtube such that the wire loop is extended about 0.5 centimeters beyond the distal end thereof. Under endoscopic viewing, the forceps grasps the loop and pulls the entire mechanism (i.e., the stiffening apparatus and jtube) toward the pylorus. The jtube is then advanced into and positioned within the small bowel. The stiffening apparatus facilitates the placement of the jtube because the increased stiffness of the jtube makes the jtube much easier to drag or push through tissue. Once the jtube is positioned within the small bowel, the endoscope is used to observe the forceps as it is opened and the loop of the stiffening apparatus is retracted into the jtube. The forceps is then retracted from the small bowel. The c-plug is then separated into two halves and removed. The endoscope and forceps are subsequently removed from the small bowel, and the stiffening apparatus is removed from the jtube.

An object of the present invention is to further provide a jtube having a distal curled end that provides a spring like mechanism to anchor the jtube within the small bowel and prevent dislodgement during removal of the forceps and stiffening apparatus.

Another object of the present invention is to provide a stiffening apparatus having a means of grasping and pulling the jtube tip. The stiffening apparatus also provides a means of stiffening jtube during placement procedure. The stiffening apparatus is disposed through a jtube and is extendable therefrom, and is configured to be withdrawn into the jtube to provide a means of separating the feeding tube tip from a grasping device, such as a forceps, without causing dislodgement of said jtube.

Another object of the present invention is to provide a stiffening apparatus having a hydrophilic coating on the outer surface thereof to facilitate removal of the stiffening apparatus from the jtube.

Another object of the present invention is to provide a stiffening apparatus that fills the space in within the lumen of the jtube. Eliminating any gaps between the jtube and stiffening apparatus will enhance the support provided by the stiffening apparatus and prevent mucus or bodily fluids from entering the jtube during placement.

Another object of the present invention is to provide a stiffening apparatus that provides a means of straightening the anchoring coil mechanism of a coiled jtube prior to the placement thereof.

Another object of the present invention provides a c-plug having a means of stabilizing a jtube disposed there through, and further having a means for centering the jtube within a PEG tube while maintaining insufflation of the stomach. The c-plug is also configured to fill the space between a jtube outer diameter and a PEG tube inner diameter.

Another object of the invention is to provide a c-plug that is removable by splitting device into separate components after use. In one embodiment, the c-plug is comprised of two halves to make whole device. This allows the c-plug to be removed without having to remove a jtube extending there through.

Other objects and advantages of the present invention will become apparent from the following descriptions, taken in connection with the accompanying drawings, wherein, by way of illustration and example, an embodiment of the present invention is disclosed.

BRIEF DESCRIPTION OF THE DRAWINGS

The drawings constitute a part of this specification and include exemplary embodiments of the present invention. It is to be understood that in some instances various aspects of the invention may be deleted for clarity, or may not be shown to scale to facilitate an understanding of the invention.

DETAILED DESCRIPTION OF THE PREFERRED EMBODIMENTS

In accordance with a preferred embodiment of the invention, there is disclosed a device and method for placing Jejunal feeding tube, also referred to as a jtube, through the stomach and into the small intestine comprising: a Jejunal feeding tube having a spring mechanism that is curled to a diameter that is similar to the diameter of the small bowel, wherein the spring mechanism can be straightened during placement. An exemplary embodiment of the Jejunal feeding tube is shown in FIGS. 7A-C and 8.

Figure 7A:
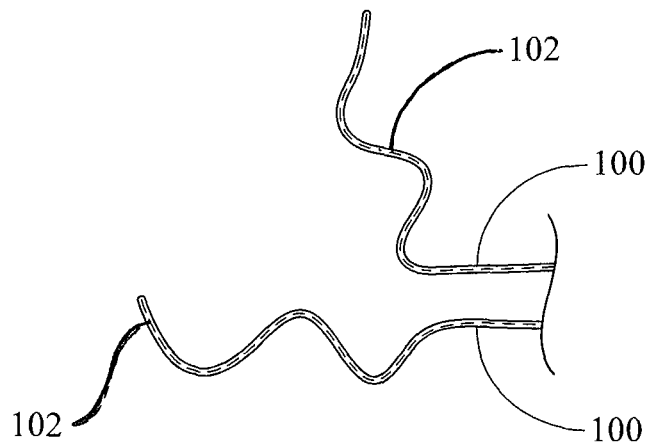
FIGS. 7A-C illustrate an exemplary Jejunal feeding to in accordance with the present invention.
Figure 8:
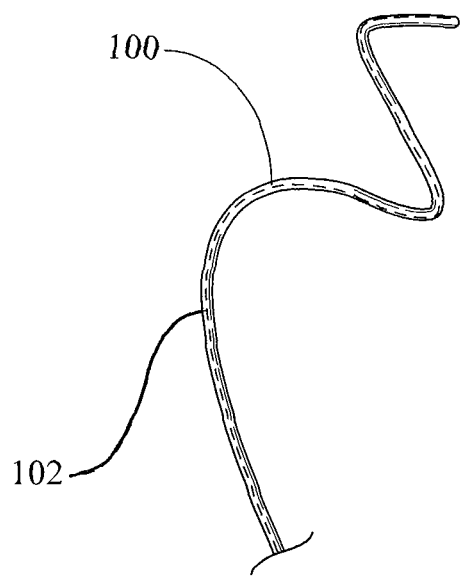
FIG. 8 illustrates the distal end of an exemplary Jejunal tube having a curled or spiral configuration in accordance with the present invention.

FIG. 7A illustrates the distal end portion of a pair of jtubes 100 each having a spring mechanism 102 comprising a coiled or spiral shape. FIG. 8 illustrates an enlarged view of the spring mechanism, i.e., the coiled distal end portion 102 of jtube 100. The diameter of the coil or spiral is preferably sized to be equal or slightly larger than the inside diameter of the small bowel to help anchor the distal end portion of the jtube 100 there within.

Figure 7B:
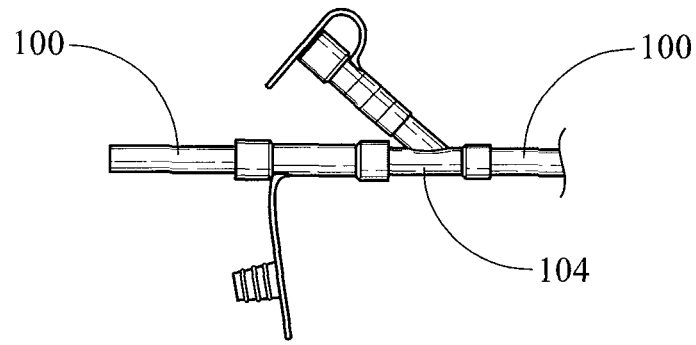

FIG. 7B illustrates the proximal end portion 104 of the jtube 100. In the particular embodiment illustrated, the proximal end portion 104 comprises a pair of ports. One of these ports is configured for the advancement of a stiffening member 110 there through, while the other port is configured for the passage of nutrients or fluids such as saline.

Figure 7C:
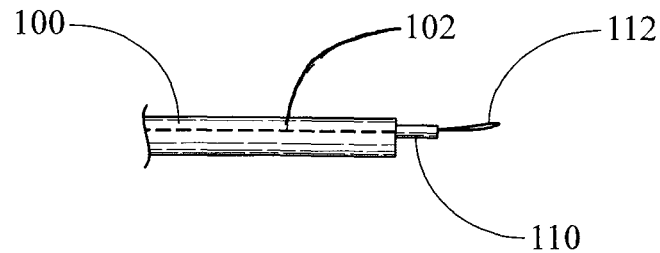

FIG. 7C illustrates the distal end portion of jtube 100 with a stiffening member 110 extending there through. The stiffening member 110 straightens the coil of the spring mechanism 102 to facilitate placement of the jtube 100 into the small bowel. The stiffening member 110 includes a loop or hook 112 on the distal end thereof for grasping by a forceps.

Figure 9:
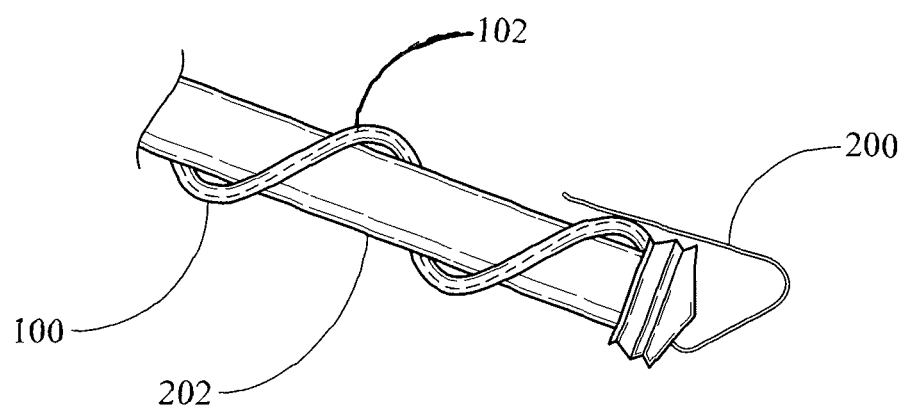
FIG. 9 illustrates a method and system for forming an exemplary Jejunal feeding tube having a curled or spiral configuration in accordance with the present invention.

FIG. 9 illustrates an exemplary method of forming a jtube 100 having a curled or spiral distal end. A forming wire 200 is provided having a spiral shape with the desired pitch and diameter. The forming wire 200 is then inserted into the distal end of the jtube 100 for the desired length. The jtube 100 with forming wire 200 inserted therein is then disposed over a heating element 202. The jtube 100 is then heated sufficiently to set the spiral shape. The forming wire 200 may then be removed. Other methods of forming a spiral shape in the distal end of the jtube 100 are well known in the art.

Figure 10:
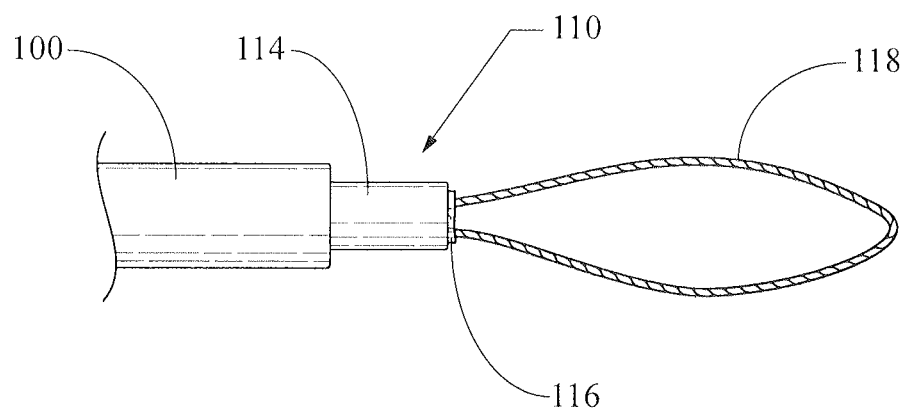
FIG. 10 illustrates the distal end portion of a stiffening apparatus having a retractable loop extending from the distal end of a Jejunal feeding tube in accordance with the present invention.
Figure 11A:
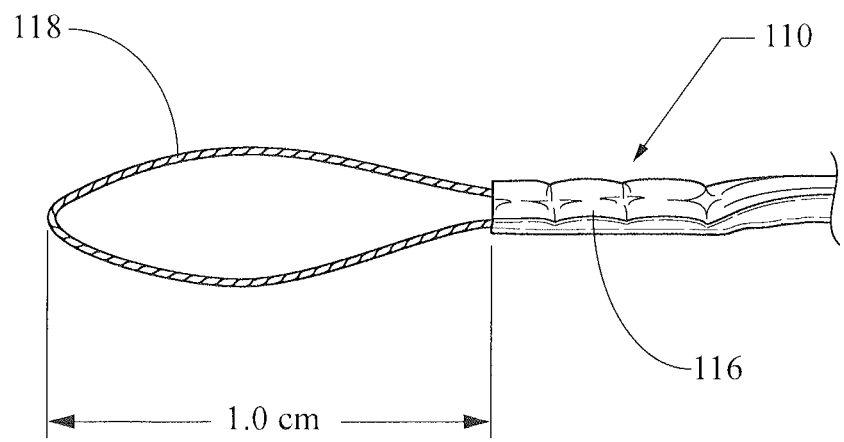
FIG. 11A illustrates distal end portion of a stiffening apparatus having a retractable loop in accordance with the present invention.
Figure 11B:
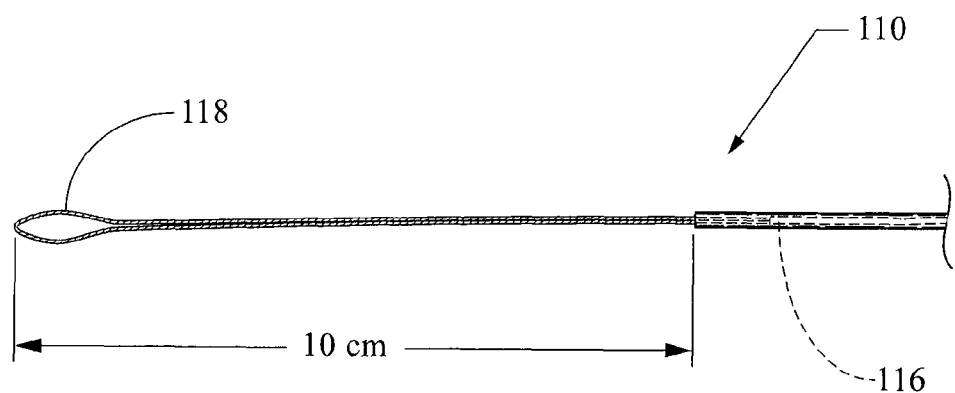
FIG. 11B illustrates an alternative embodiment of a stiffening apparatus having a retractable loop in accordance with the present invention.
Figure 12:
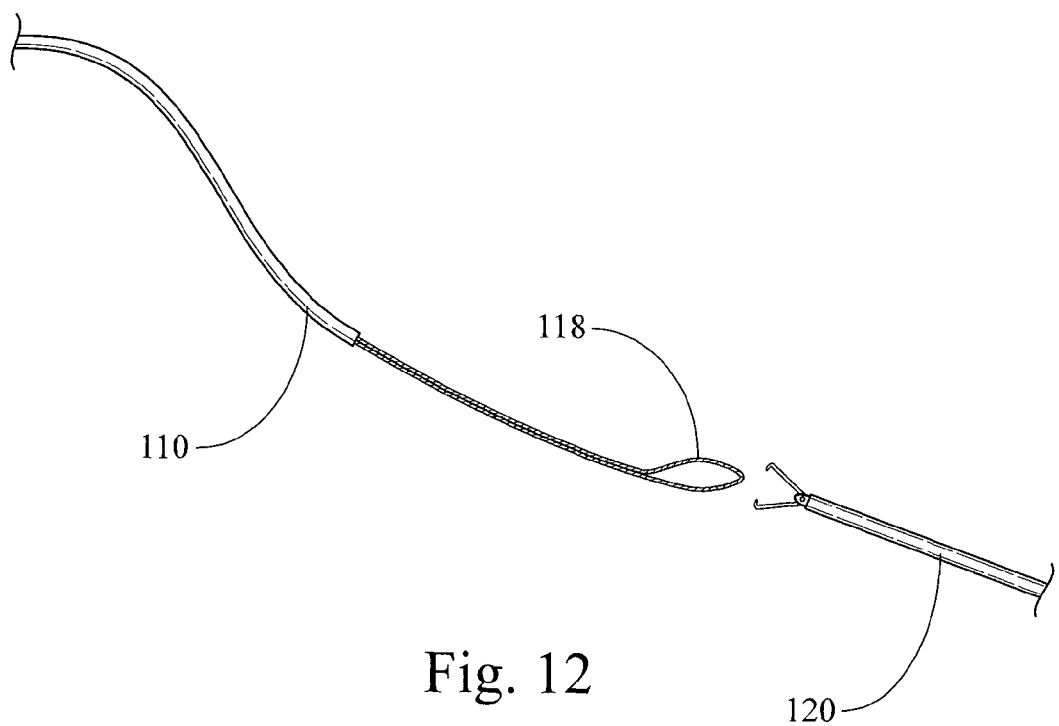
FIG. 12 illustrates a grasping forceps in combination with a stiffening apparatus in accordance with the present invention.

As explained above, the spring mechanism 102 of the jtube 100 may be straightened with a stiffening apparatus 110 to facilitate placement thereof, wherein the stiffening apparatus is guided by a grasping device such as a forceps. Embodiments of the stiffening apparatus 110 are illustrated in FIGS. 10 and 11A-B. The stiffening apparatus 110 includes a wire loop 118 affixed to the distal end of a mandrel 116. The wire loop 118 is configured to be gasped by a forceps 120 (see FIG. 12) during placement of the jtube 100. The mandrel 116 supports the jtube 100 and straightens the spring mechanism 102 during placement of the jtube 100 within the small bowel.

The overall length of the stiffening apparatus 110, which is the combined length of the mandrel 116 and the wire loop 118, is longer than the overall length of the jtube 100 such that at least a portion of the wire loop 118 extends beyond the distal end of the jtube 100, whereby it may be grasped by a forceps or other device. In the preferred embodiment, the length of the stiffening apparatus 110 is configure such that the loop 118 extends approximately 0.5 cm beyond the distal end of the jtube 100 when the stiffening apparatus 110 is fully advanced there through.

In the embodiment illustrated in FIG. 11A, the wire loop 118 comprises a length of about 0.7 cm to 1 cm. In the embodiment illustrated in FIG. 10B, the wire loop 118 comprises a length of about 10 cm. Accordingly, the length of the mandrel 116 is shorter for the embodiment of FIG. 11B as compared to the embodiment of FIG. 11A. Because of the shorter length of the mandrel 116 of the embodiment of FIG. 11B, the distal end of the mandrel 116 terminates proximally of the distal end of the jtube 100 when fully advanced there through. This increases the flexibility of the distal end of the jtube 100, thereby reducing the possibility that the distal end of the jtube 100 will puncture or harm tissue during placement thereof. The increased flexibility also facilitates advancement of the jtube 100 into and through the pylorus and reduces the chance of perforation.

As best seen in FIG. 10, the stiffening apparatus 110 may include a catheter 114 disposed over the mandrel 116. The catheter 114 increases the diameter of the stiffening apparatus 110 to more closely match the inside diameter of the jtube 100. This may help to prevent or limit contamination of the jtube 100 during placement. The catheter 114 may also be used to increase, decrease or otherwise alter the stiffness of the stiffening apparatus 100. For example, during placement of the jtube 100 it may be necessary to increase the flexibility of the distal end of the jtube 100. This may be accomplished by retracting catheter 114 relative to the stiffening apparatus 110 and jtube 100. Likewise, catheter 114 may be advanced relative to these components to increase stiffness. Catheter 114 may also be used to assist in separating a forceps from the wire loop 118 by advancing the catheter 114 over and past the distal end of the loop 118.

In the preferred embodiment, the stiffening apparatus 110 comprises a hydrophilic coating. The hydrophilic coating may be applied to the exterior surface of the mandrel 116 and/or the catheter 114. The hydrophilic coating helps to prevent the stiffening apparatus 110 from dislodging the jtube 100 during removal.

Figure 13:
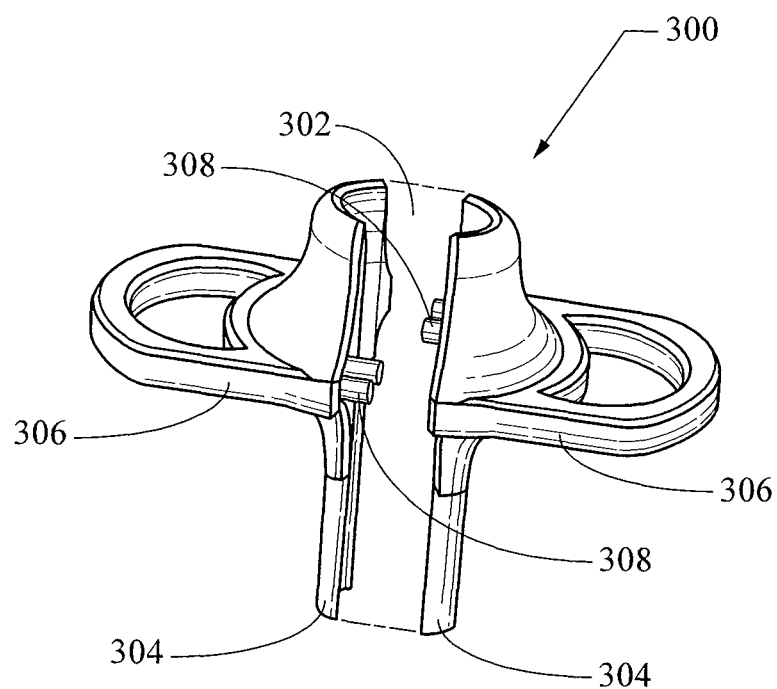
FIG. 13 illustrates a c-plug in accordance with the present invention in an open or separated position.
Figure 14:
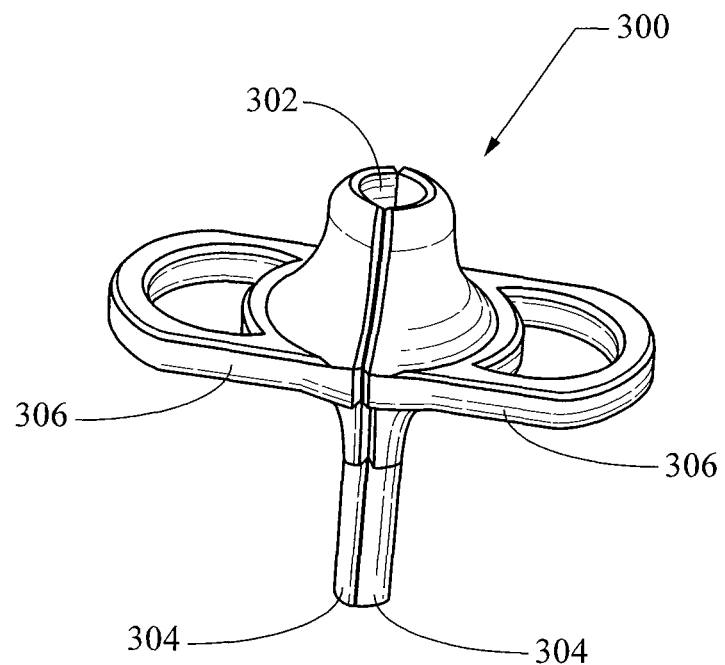
FIG. 14 illustrates a c-plug in accordance with the present invention in a closed or connected position.

Also disclosed is a c-plug for centering the Jejunal feeding tube (jtube) during the placement procedure. An exemplary embodiment of the c-plug 300 is shown in FIGS. 13-14. The c-plug 300 includes a lumen 302 through which a jtube may be advanced. The lumen 302 of the c-plug 300 has an inner diameter that is configured to accommodate a jtube there through, and is preferably configured to seal about the jtube so as to maintain insufflation of the stomach. The c-plug 300 also includes a distal tubular member 304 having an outer diameter that is configured for insertion into a PEG tube (not shown), and is preferably configured to form a seal therewith.

In exemplary embodiment illustrated, the c-plug 300 comprises two separable halves 306 to allow the c-plug 300 to be laterally removed after jtube placement. As illustrated in FIG. 13, each halve 306 may include a mating elements 308 to align and secure the halves 306 together. The ability to separate the c-plug 300 into two components or halves 306 facilitates removal of the c-plug from the PEG tube and jtube.

Figure 1:
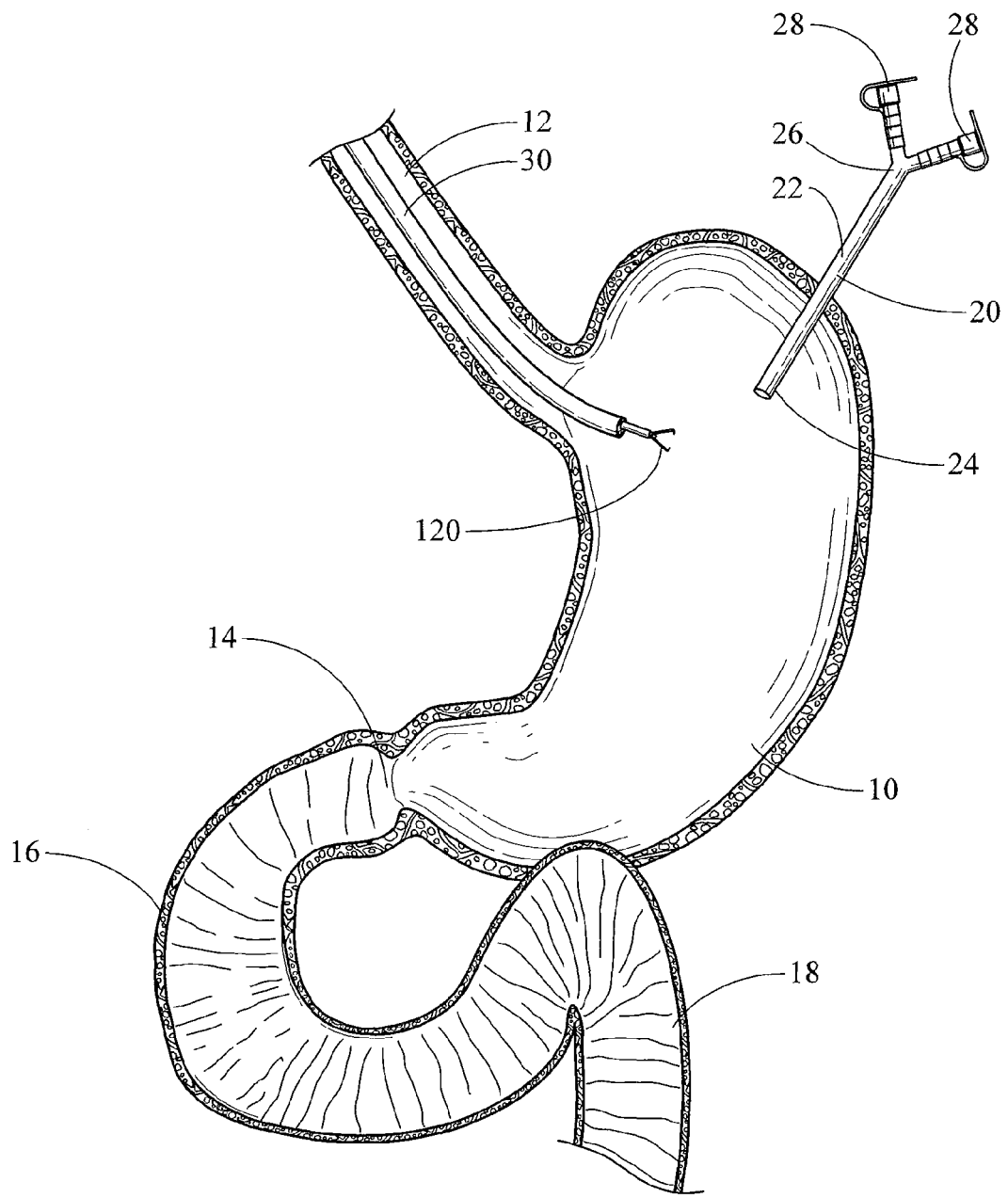
FIGS. 1 to 6 illustrate sequential steps in an exemplary method of the present invention.

An exemplary method of placing a Jejunal feeding tube in accordance with the present invention is illustrated in FIGS. 1-6. FIG. 1 illustrates a portion of the gastrointestinal system of a mammalian patient comprising a stomach 10, esophagus 12, pylorus 14, duodenum 16 and jejunum or small intestine (small bowel) 18. A gastrostomy or PEG tube 20 of conventional construction is percutaneously inserted into the stomach 10. The PEG tube 20 comprises a tubular member 22 having a distal end 24 disposed within the stomach 10, and one or more feeding lumens extending there through. The proximal end 26 of the PEG tube 20 comprises connectors 28 adapted to connect to a nutrient supply source, such as an IV set or syringe. The connectors 28 typically include caps to close the connectors 28 when not in use and to prevent contamination thereof. FIG. 1 also illustrates an endoscope 30 being advance through the esophagus 12 and into the stomach 10. A grasping device, such as forceps 120, is shown extending distally from the distal end of the endoscope 30.

Figure 2:
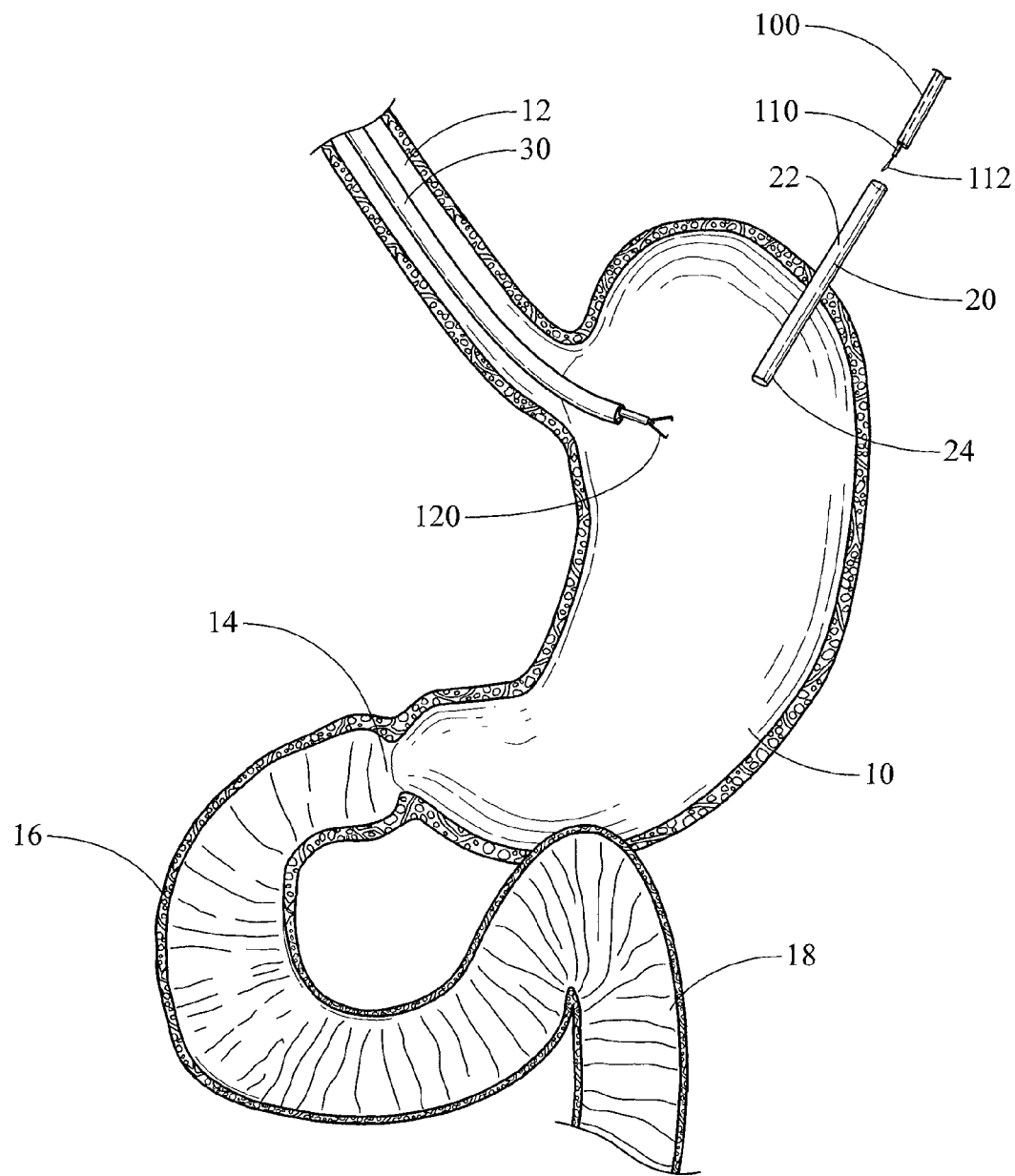

FIG. 2 illustrates the step of advancing a Jejunal feeding tube (jtube) into and through the PEG tube 20. In the preferred embodiment illustrated, the jtube 100 is of the type illustrated in FIGS. 7A-8 and includes a stiffening apparatus 110 disposed there through. The stiffening apparatus 110 is generally of the type illustrated in FIGS. 10-11B, and has been advanced through the jtube 100 a sufficient distance so as to extend the wire loop 112 beyond the distal end of the jtube 100. Prior to inserting the jtube 100 into the PEG tube 20, the proximal end 26 and connectors 28 of the PEG tube may be cut and removed therefrom. Alternatively, the proximal end 2 and connectors 28 may be retained and the jtube 100 may be advance through one of the connectors 28.

Figure 3:
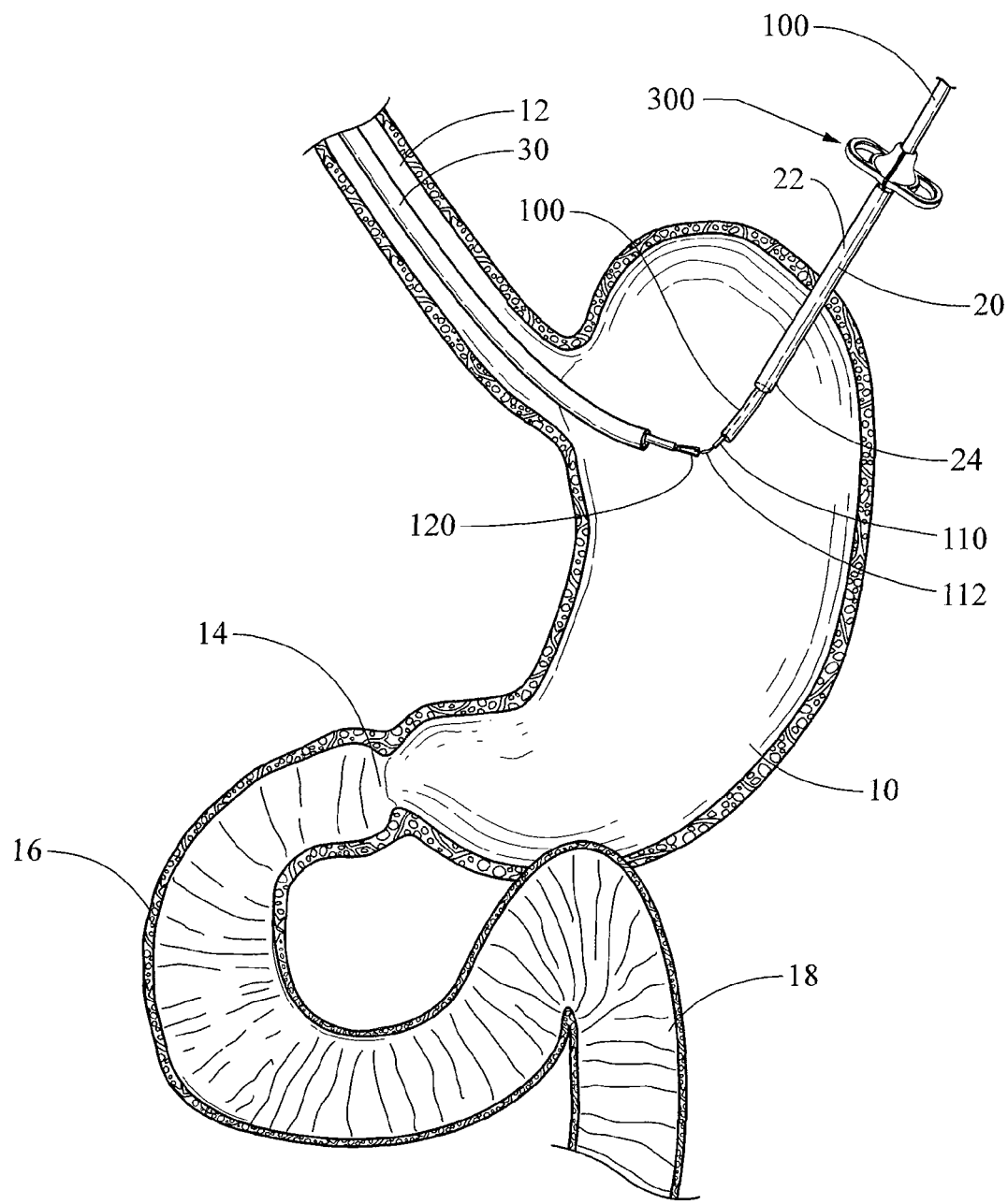

FIG. 3 illustrates the distal end of the jtube 100 extending distally of the distal end 24 of the PEG tube 20 and into the stomach 10. A c-plug 300 of the type illustrated in FIGS. 13-14 is subsequently disposed about the jtube 100 and inserted to the lumen of the PEG tube 20 to thereby create a seal between these components. The stomach 10 is then insufflated to enable the endoscope 30 to view the wire loop 112 of the stiffening apparatus 110, and to enable the wire loop 112 to be grasped by the forceps 120.

Figure 4:
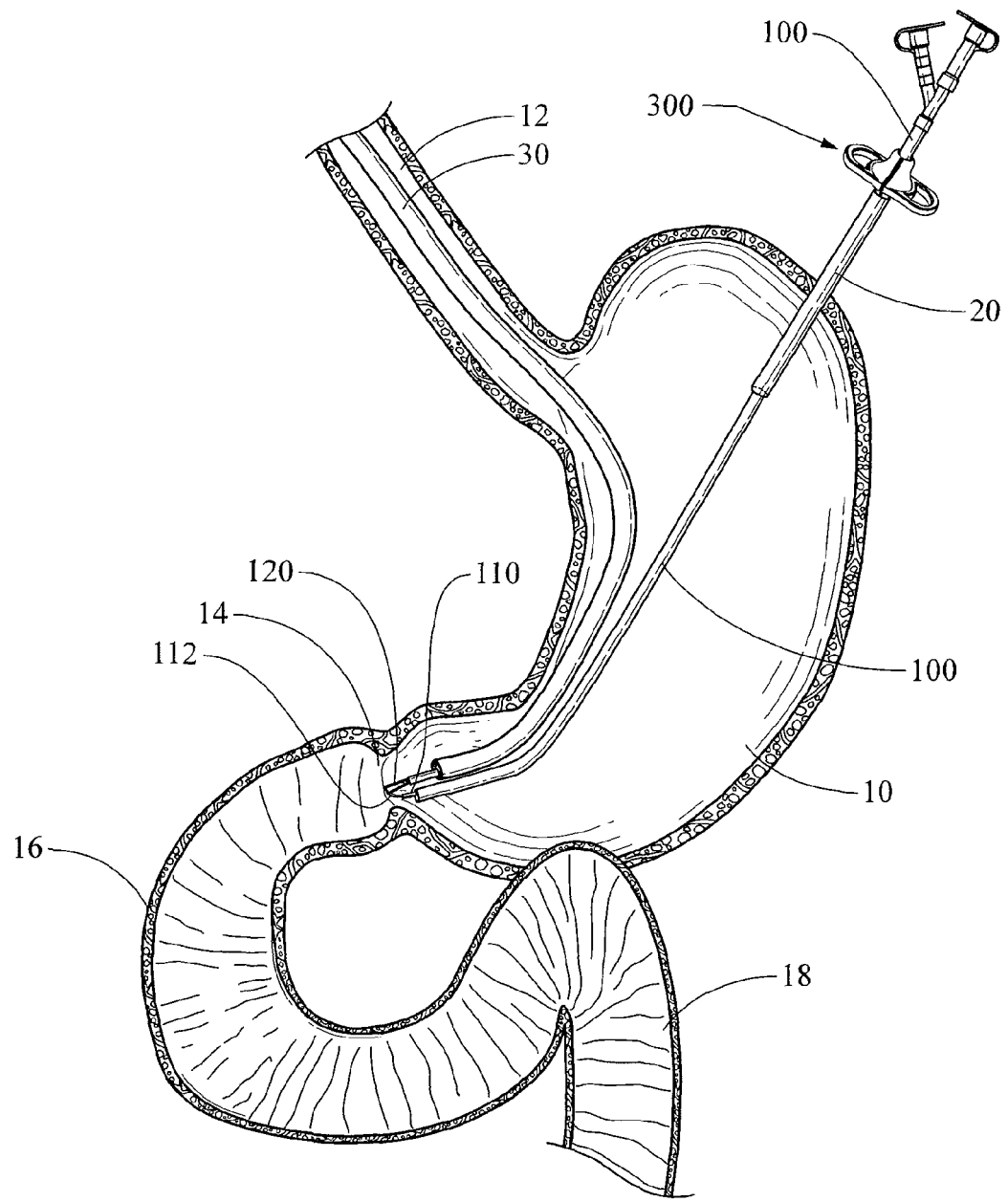

FIG. 4 illustrates the jtube 100 being dragged by the endoscope 30 and forceps 120 towards into the pylorus 14 and towards the duodenum 16. If necessary, the flexibility of the stiffening apparatus 110 may be altered to facilitate advancement thereof by, for example, retracting catheter 114 of the stiffening member 110 (see FIG. 10) proximally to increase the flexibility of the distal end portion of the jtube 100.

Figure 5:
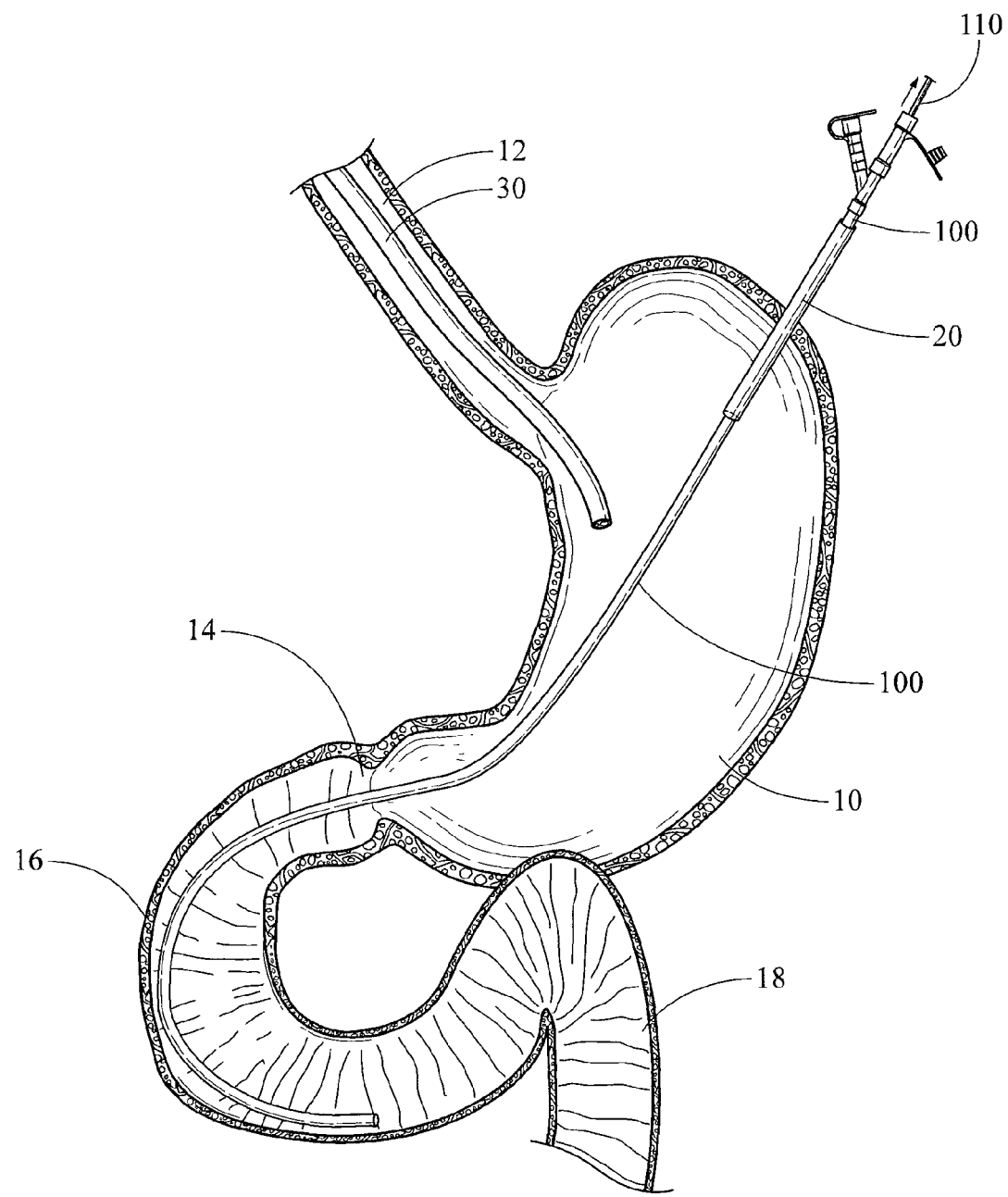

FIG. 5 illustrates the jtube 100 advanced through the pylorus 14 and into the small bowel 18. The forceps 120 is disconnected from the wire loop 112 of the stiffening apparatus and removed. In the preferred method, the jaws of the forceps 120 are opened while the stiffening apparatus 110 is withdrawn proximally to retract the wire loop 112 into the lumen of the jtube 100. This causes complete separation of the jaws of the forceps 120 from the wire loop 112. Alternatively, the catheter 114 of the stiffening apparatus 100 (see FIG. 10) can be advanced distally beyond the distal end of the wire loop 112 to separate the wire loop 112 from the forceps 120. The stiffening apparatus 110 is remains disposed within the jtube 100 to provide support thereto and prevent the jtube 100 from becoming dislodged from the small bowel 18. The endoscope 30 and the c-plug 300 can be removed.

Figure 6:
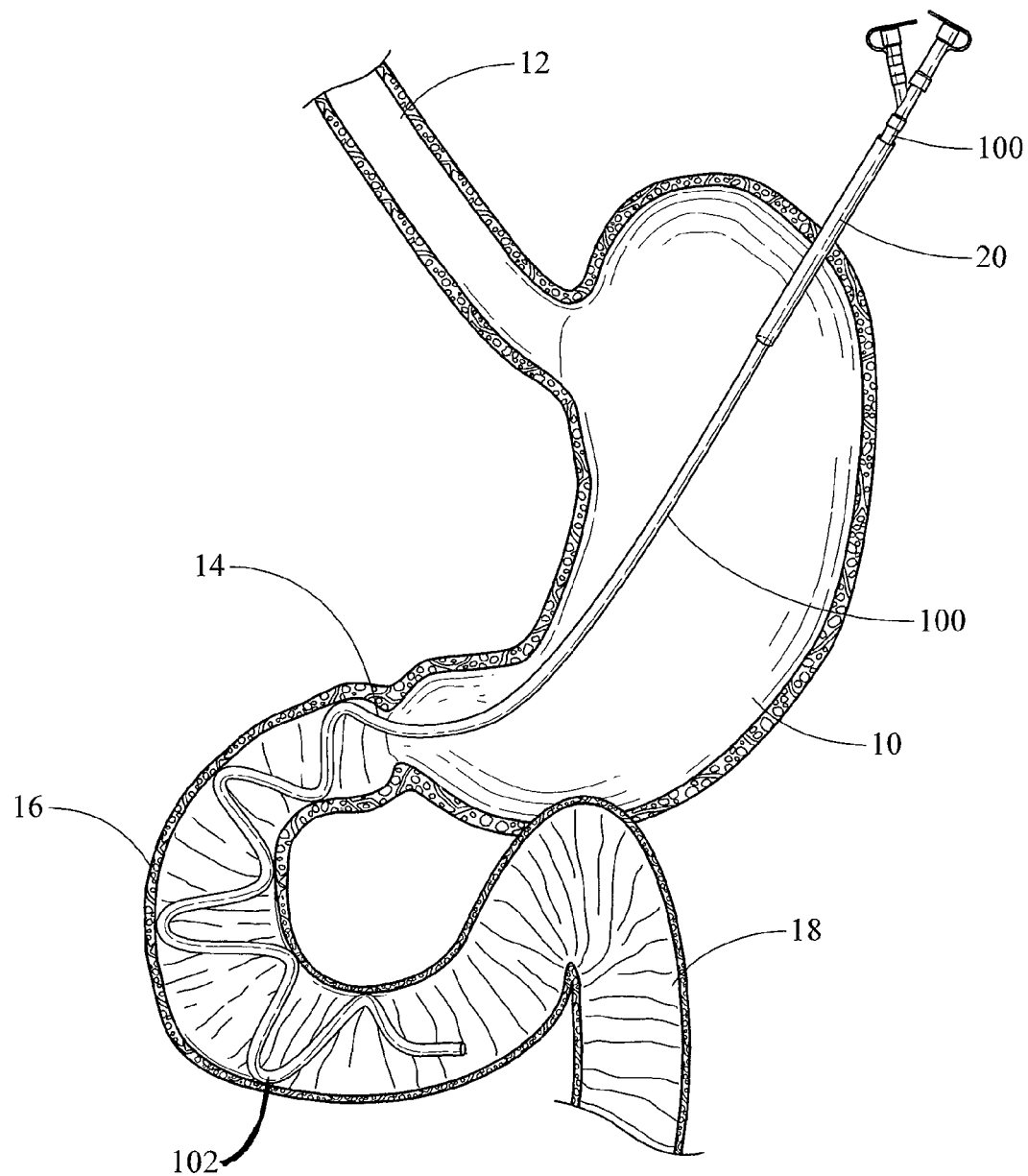

FIG. 6 illustrates the jtube 100 in its final position within the small bowel 18. First, the stiffening apparatus 110 is partially retracted in a proximal direction a sufficient distance to allow the spring mechanism 102 on the distal end of the jtube 100 to assume a spiral or coiled configuration. The spring mechanism 102 anchors the distal end of the jtube 100 within the small bowel 18. Once the jtube 100 is properly anchored, the stiffening member 110 may be completely removed therefrom.

An exemplary step-by-step method of placing a Jejunal feeding tube in accordance with the present invention is set forth as follows:
1. Scope Patient;
2. Flush the port and lumen of the Jejunal feeding tube (jtube) with sterile water;
3. Insert the stiffening apparatus through the port and into the lumen of the jtube;
4. Advance the stiffening apparatus through the lumen of the jtube sufficiently to extend the wire loop of the stiffening apparatus beyond the distal end of the jtube;
5. Lubricate the exterior surface of the jtube;
6. Remove the loading adaptor from the jtube;
7. Load the c-plug onto the jtube, and then slide jtube and PEGJ and c-plug into the PEG tube;
8. Re-inflate the stomach;
9. Advance the forceps through the scope channel of the endoscope and into the stomach;
10. Grasp the wire loop of the stiffening apparatus with the forceps;
11. Maintain the forceps, stiffening apparatus and jtube close to the end of endoscope to ease guidance thru the pylorus;
12. Push the endoscope (and forceps, stiffening apparatus and jtube) into and through the duodenum, i.e., beyond the duodenal c loop until straight portion of the small bowel is seen;
13. While viewing with the endoscope, advance the forceps, stiffening apparatus and jtube towards the small bowel (Jejunum);
14. Remove the c-plug and continue advancing forceps, stiffening apparatus and jtube until J adapter (connector) of the jtube seats into PEG tube (external);
15. Release the wire loop of the stiffening apparatus from the forceps and slowly remove the forceps from the endoscope and patient;
16. Observe with the endoscope and verify that the jtube has maintained its position and has not been dislodged by the removal of the forceps;
17. Withdraw the endoscope so as to position the distal end thereof within the stomach;
18. Remove the stiffening apparatus from the jtube;
19. Observe with the endoscope and verify that the jtube has not become dislodged or coiled within stomach; and
20. Remove the endoscope completely from the patient.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A kit for placing a jejunal feeding tube through the stomach and into the small intestine of a patient, the kit comprising:
   jejunal feeding tube comprising a tubular member extending from a proximal end to a distal end, a feeding lumen extending through the tubular member, the proximal end comprising a connector configured for attachment to a source of nutrients, the distal end comprising a spring mechanism configured to engage the walls of the small intestine and anchor the distal end therein, the spring mechanism comprising one or more spiral shaped coils;
   an elongate stiffening apparatus removably disposed through the feeding lumen of the jejunal feeding tube, the stiffening apparatus comprising an elongate mandrel with a wire loop disposed on a distal end thereof, the wire loop extending distally beyond the distal end of the tubular member and configured to be grasped by a grasping device, the stiffening apparatus being configured to temporarily straightening the spring mechanism of the jejunal feeding tube when disposed there through; and
   a c-plug removably disposed about the jejunal feeding tube, the c-plug configured to provide a seal between the jejunal feeding tube and a percutaneous endoscopic gastrostomy ("PEG") feeding tube when the jejunal feeding tube is disposed through a lumen of the PEG feeding tube, the c-plug comprising a tubular extension having an outer diameter configured to fit into the lumen of the PEG feeding tube, the tubular extension having an inner diameter configured to fit around the tubular member of the jejunal feeding tube.

2. The kit according to claim 1 wherein the jejunal feeding tube comprises an overall length of at least 65 inches.

3. The kit according to claim 1 wherein the spiral shaped coils of the spring mechanism comprises an overall length of between 0.75 inches to 2 inches.

4. The kit according to claim 1 wherein the spring mechanism comprises between 1 and 4 spiral shaped coils.

5. The kit according to claim 1 wherein the spring mechanism is movable between a straightened configuration when the stiffening apparatus is disposed there through, and a coiled configuration when the stiffening apparatus is not disposed there through.

6. The kit according to claim 1 wherein the wire loop of the stiffening apparatus has a length of between 0.7 cm and 1 cm.

7. The kit according to claim 1 wherein the mandrel of the stiffening apparatus comprises a length that is less than the length of the tubular member of the jejunal feeding tube.

8. The kit according to claim 7 wherein the wire loop of the stiffening apparatus has a length of between 1 cm and 10 cm.

9. The kit according to claim 1 wherein the stiffening apparatus further comprises a catheter movably disposed about the mandrel.

10. The kit according to claim 9 wherein the catheter is configured to be advanced over the wire loop.

11. The kit according to claim 1 wherein the stiffening apparatus comprises an overall length that is about 0.5 cm to 1 cm greater than an overall length of the jejunal feeding tube.

12. The kit according to claim 1 wherein the stiffening apparatus comprises a hydrophilic coating disposed on an outer surface thereof.

13. The kit according to claim 1 wherein the c-plug is separable into two halves to permit lateral removal from the jejunal feeding tube.

14. A method of placing a jejunal feeding tube through an indwelling percutaneous endoscopic gastrostomy ("PEG") feeding tube and into the small intestine of a patient, the method comprising the steps of:
   providing a jejunal feeding tube comprising a tubular member extending from a proximal end to a distal end, a feeding lumen extending through the tubular member, the proximal end comprising a connector configured for attachment to a source of nutrients, the distal end comprising a spring mechanism configured to engage the walls of the small intestine and anchor the distal end therein, the spring mechanism comprising one or more spiral shaped coils;

providing an elongate stiffening apparatus comprising an elongate mandrel with a wire loop disposed on a distal end thereof;

disposing the stiffening apparatus through the tubular member of the jejunal feeding tube such that the wire loop extends distally beyond the distal end of the tubular member, and such that the stiffening apparatus temporarily straightens the spring mechanism of the jejunal feeding tube;

advancing the jejunal feeding tube and stiffening apparatus simultaneously through the indwelling PEG feeding tube and into the patient's stomach;

extending a forceps through an endoscope and into the patient's stomach, and then grasping the wire loop of the stiffening apparatus with the forceps;

dragging the stiffening apparatus and jejunal feeding tube with the forceps into the patient's small intestine;

disconnecting the forceps from the wire loop;

retracting the stiffening apparatus in a proximal direction relative to the jejunal feeding tube until the wire loop is fully disposed within the feeding lumen of the jejunal feeding tube;

retracting the forceps from the patient's small intestine;

removing the stiffening apparatus from the jejunal feeding tube; and removing the forceps and the endoscope from the patient.

15. The method according to claim 14 further comprising the step of removably disposing a c-plug disposed about the jejunal feeding tube and inserting the c-plug into the PEG feeding tube so as to provide a seal between the jejunal feeding tube and a PEG feeding tube prior to the step of grasping the wire loop of the stiffening apparatus with the forceps.

16. The method according to claim 14 further comprising the subsequent step of separating the c-plug into a plurality of components and laterally removing the components from the jejunal feeding tube.

* * * * *